(12) United States Patent
Slautterback

(10) Patent No.: US 6,740,056 B2
(45) Date of Patent: *May 25, 2004

(54) UNIVERSAL SIZED CARPAL TUNNEL DEVICE

(75) Inventor: E. Gerald Slautterback, Coral Springs, FL (US)

(73) Assignee: FLA Orthopedics, Inc., Miramar, FL (US)

( * ) Notice: Subject to any disclaimer, the term of this patent is extended or adjusted under 35 U.S.C. 154(b) by 106 days.

This patent is subject to a terminal disclaimer.

(21) Appl. No.: 09/946,070

(22) Filed: Sep. 4, 2001

(65) Prior Publication Data

US 2002/0062095 A1 May 23, 2002

Related U.S. Application Data

(63) Continuation-in-part of application No. 09/677,210, filed on Oct. 2, 2000, now Pat. No. 6,517,501.

(51) Int. Cl.[7] ................................................. A61F 5/00
(52) U.S. Cl. ............................. 602/21; 602/64; 128/879
(58) Field of Search ........................... 602/5, 21, 61, 602/62, 64; 128/878, 879; 2/16, 20; 5/646, 647; 682/44–45

(56) References Cited

U.S. PATENT DOCUMENTS

| | | | |
|---|---|---|---|
| 1,377,103 A | * | 5/1921 | Suhr ................................ 2/16 |
| 4,531,241 A | | 7/1985 | Berger |
| 4,850,341 A | | 7/1989 | Fabry et al. |
| 5,160,314 A | | 11/1992 | Peters |
| 5,214,799 A | | 6/1993 | Fabry |
| 5,267,943 A | * | 12/1993 | Dancyger ........................ 602/5 |
| 5,385,537 A | | 1/1995 | Davini |
| 5,415,624 A | * | 5/1995 | Williams ....................... 602/21 |
| 5,417,645 A | | 5/1995 | Lemmen |
| 5,468,220 A | | 11/1995 | Sucher |
| 5,652,955 A | * | 8/1997 | Skewis ............................. 2/20 |
| 5,672,150 A | * | 9/1997 | Cox .............................. 602/21 |
| 5,672,151 A | * | 9/1997 | Calderon-Garciduenas .. 602/21 |
| 5,746,707 A | | 5/1998 | Eck |
| 5,769,804 A | | 6/1998 | Harris et al. |
| 5,925,007 A | * | 7/1999 | Ashline ........................ 602/21 |
| 6,398,748 B1 | * | 6/2002 | Wilson ......................... 602/21 |

* cited by examiner

Primary Examiner—Danton D. DeMille
Assistant Examiner—Justine Yu
(74) Attorney, Agent, or Firm—Dougherty, Clements & Hofer

(57) ABSTRACT

A universal carpal tunnel device for supporting the hand in a neutral position to alleviate and prevent the carpal tunnel syndrome. The device includes a pad for placement against a wearer, a base attached to the pad, a stay disposed between the pad and base, and an adjustment strap for attaching the device to the wearer. The pad or the base can be provided with a recessed channel for receiving the stay. The pad, base and stay form a palmar section of the device which extends over the heel of the hand and terminates prior to the palmar fold of the hand so to not unnecessarily restrict movement of the wearer's hand and digits, and a main section for engaging the forearm of the wearer. The palmar section also has a sufficient width for preventing opposition between the thumb and the fifth digit of the hand. The device laterally has first and second sides which are mirror images of each other so that the carpal tunnel device can be used on either the right or left hand.

20 Claims, 6 Drawing Sheets

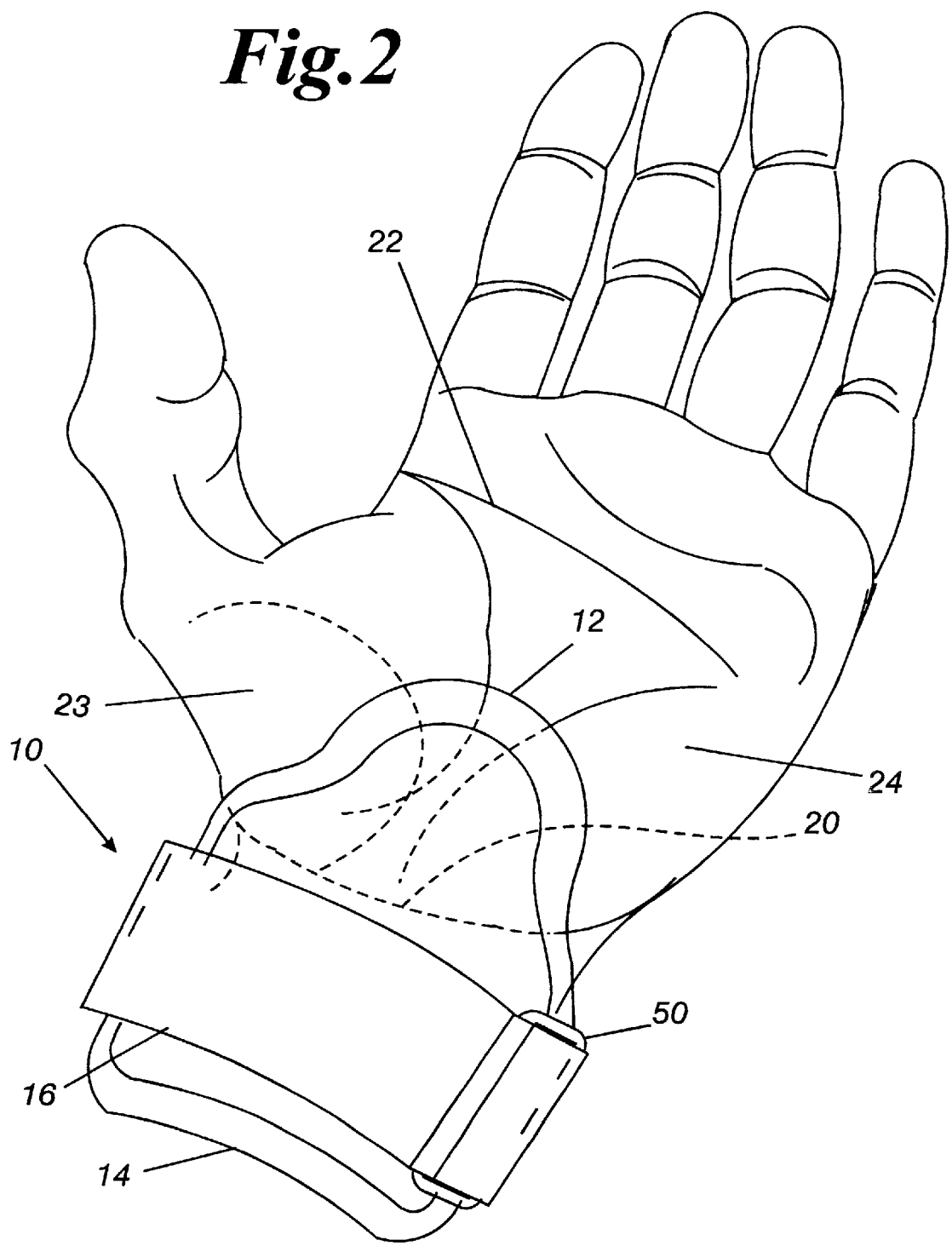

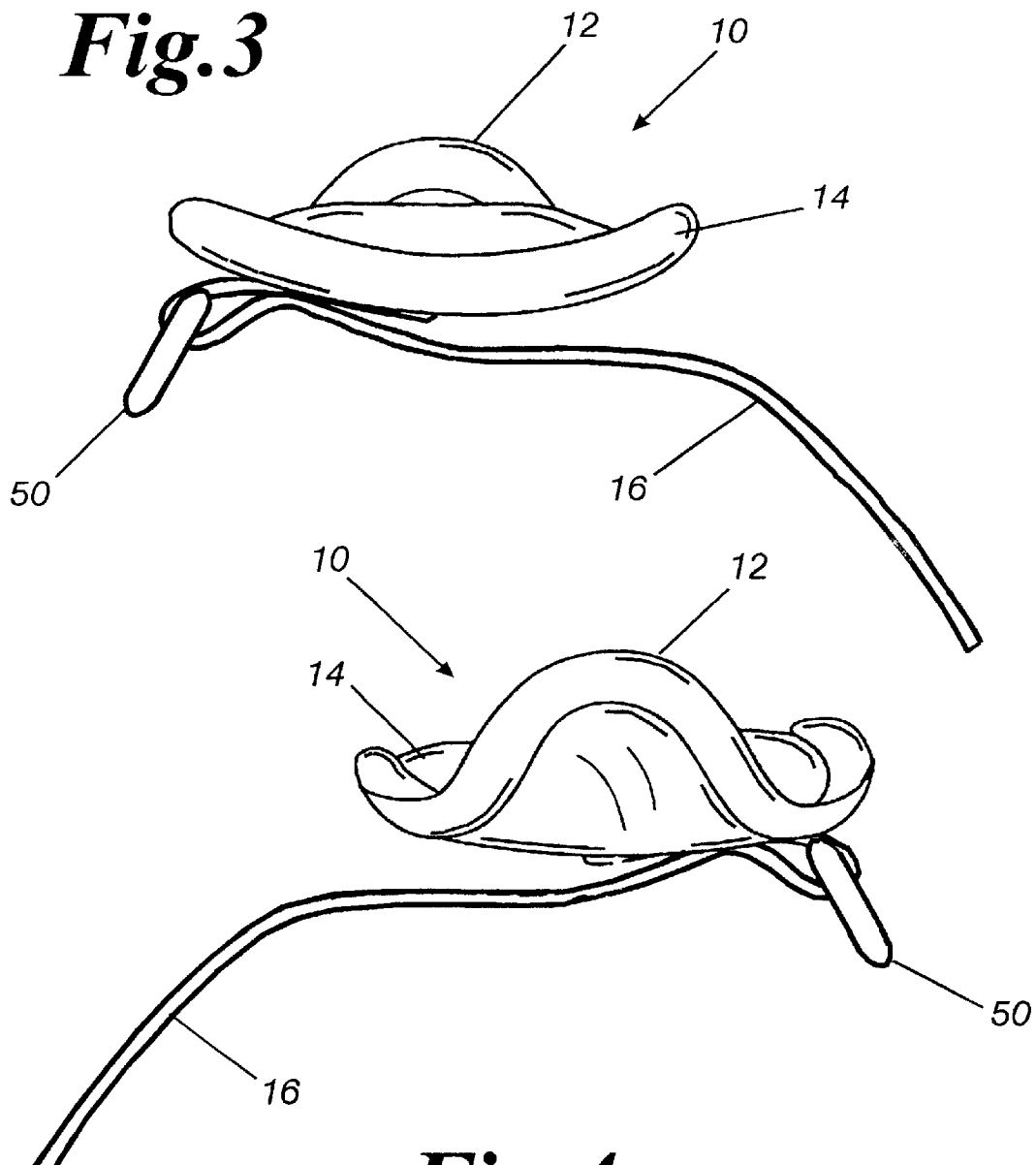

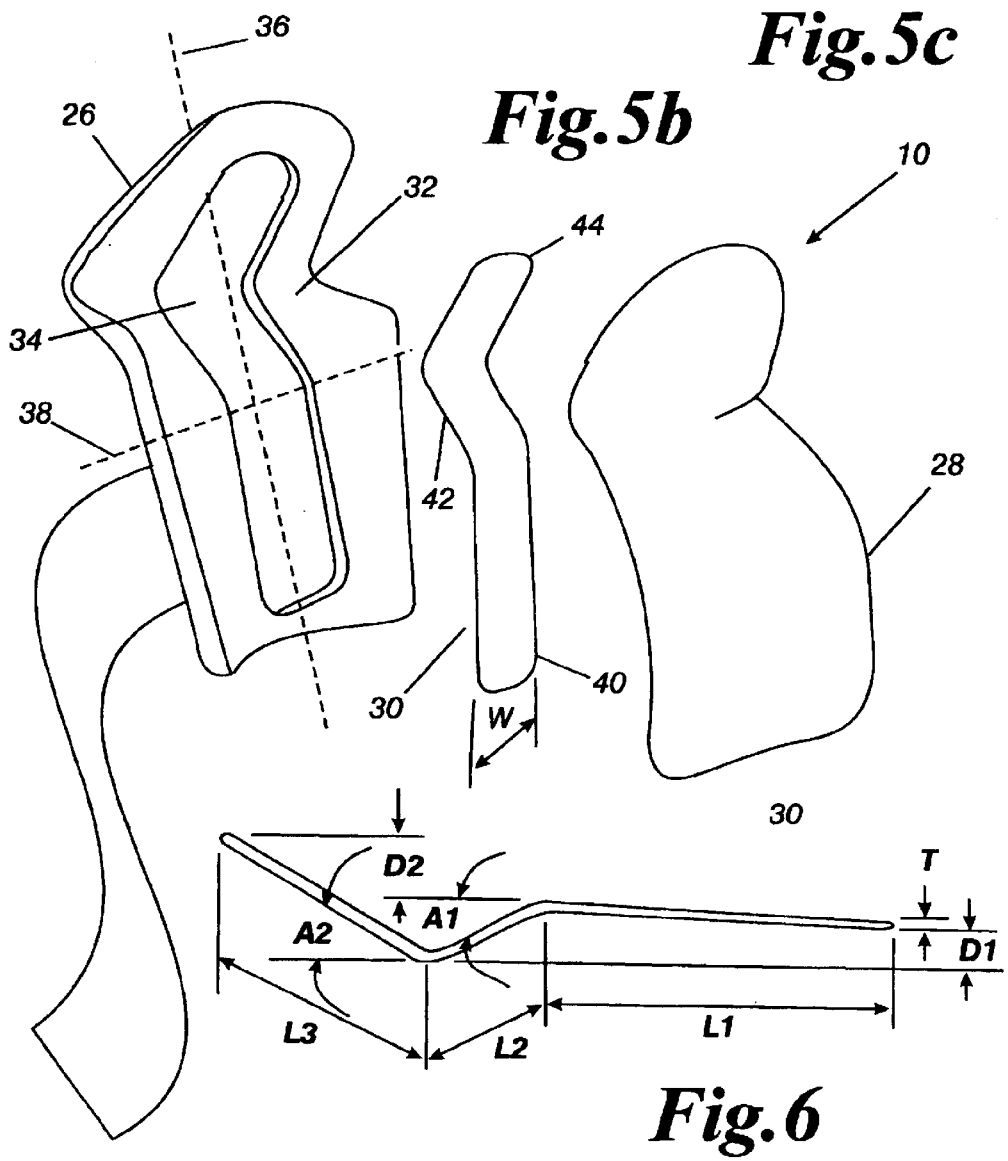

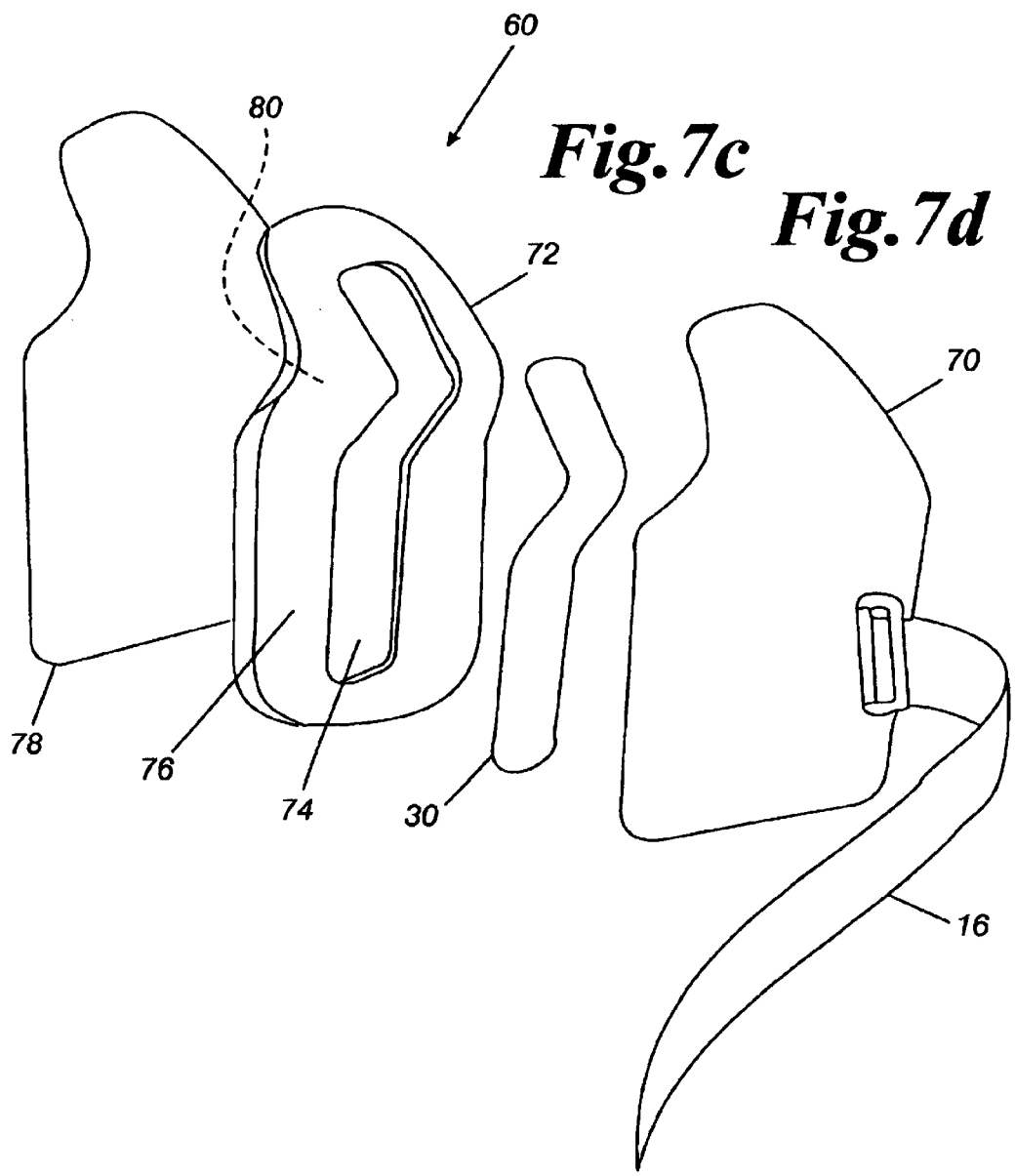

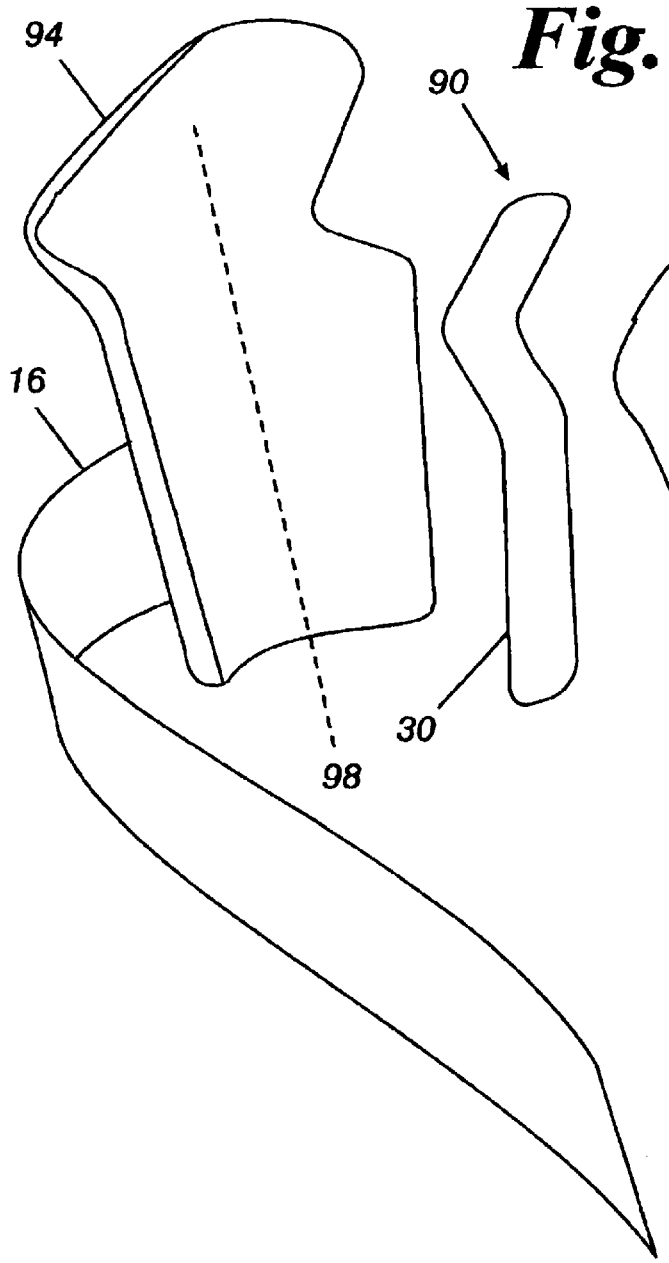
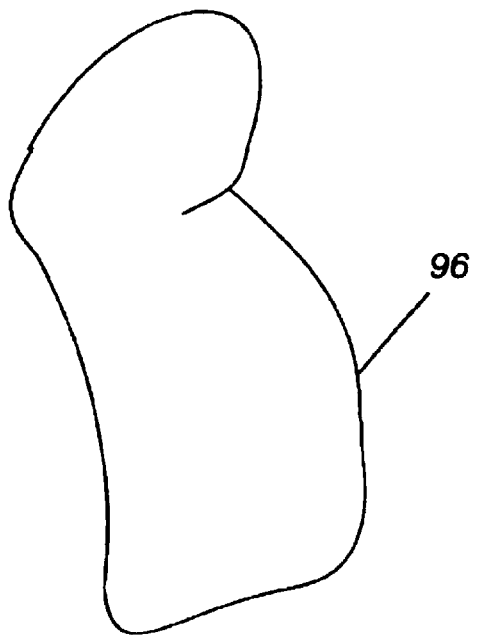
*Fig.8a*  *Fig.8b*  *Fig.8c*

US 6,740,056 B2

UNIVERSAL SIZED CARPAL TUNNEL DEVICE

CROSS REFERENCE TO RELATED APPLICATION

This application claims the benefit of U.S. Provisional Application No. 60/267,446, filed Feb. 8, 2001 (now expired), and is a Continuation in Part of U.S. application Ser. No. 09/677,210, filed Oct. 10, 2000 (issued on Feb. 11, 2003 as U.S. Pat. No. 6,517,501).

FIELD OF THE INVENTION

The present invention relates to a method and apparatus for supporting a wrist, and more particularly to a wrist support used for abating the affects of carpal tunnel syndrome.

BACKGROUND OF THE INVENTION

Carpal tunnel syndrome is a common condition of the hand caused by swelling of the synovial membrane, tendon inflammation, and any condition that reduces the available space in the carpal tunnel. Activities that cause flexion of the wrist and fingers, such as repetitive and forceful grasping of the hands and repetitive bending of the wrist, are common causes of carpal tunnel syndrome. Carpal tunnel syndrome can also be caused from injury or trauma such as blunt contusions, wrist bone dislocations and fractures which compromise the carpal tunnel, thereby resulting in pressure on the median nerve. Common symptoms of this condition include pain and numbness of the hand. Specifically, these symptoms are caused when a dense fibrous tissue called the transverse carpal ligament forms over and compresses the median nerve.

Treatment of carpal tunnel syndrome varies according to the severity of the condition. Severe conditions usually require hand surgery to sever the transverse carpal ligament. For less severe cases, the use of a splint, which immobilizes the wrist, is sometimes effective, often in combination with anti-inflammatory medication. Such treatments are generally expensive, painful and may reduce the patient's ability to use the affected hand.

Carpal tunnel syndrome is a particular problem for workers in industries which require repeated manual hand motions, such as modern day keyboard operations. In response to this problem, keyboard wrist rest and wrist devices have become ubiquitous.

The keyboard wrist rests are intended to keep the hand and wrist at about a 15° angle, which is referred to as the neutral position. However, the keyboard wrist rests provide no benefit except when the hand is placed properly thereon.

Wrist devices for the treatment or prevention of carpal tunnel syndrome include bracelets, gloves and wrist support. These devices have limitations such as being configured for use with only the left hand or the right hand, impede free motion of the hand and digits of the hand that is unrelated to carpal tunnel syndrome, are uncomfortable to wear and do not prevent the wrist from dropping below the neutral position.

Bracelets create pressure points around the wrist to alleviate carpal tunnel syndrome; however, these pressure points can be uncomfortable to the wearer. Moreover, brackets do not maintain the wrist in the neutral position.

Gloves are configured for either the right hand or the left hand to provide protection from vibrations and shocks which can cause carpal tunnel syndrome. However, the gloves may not maintain the wrist in a normal position and can impede free motion of the hand and digits.

Traditional wrist supports are adapted for either the left or right hand, and enclose the wrist and at least a portion of hand. Since the hand is partially encased, these devices unnecessarily restrict hand mobility and are uncomfortable to wear.

Additionally, wrist supports typically utilize a rigid stay to maintain the wrist in the neutral position. The stay in conventional wrist supports generally is too narrow and causes pressure points and ridge-lined surfaces which are uncomfortable, or, the stay is too wide and will not bend or conform to the circumference of the wrist.

Another problem is that the wrist device should provide support at or near the center of the hypothenar eminence, and at or near the thenar eminence in order to restrict opposition between the thumb and the fifth digit to prevent excess flexion. Narrow rigid stays do not cover the necessary surface area, while wide stays do not conform to the palm, and thus create gaps, pressure points and ridge-lines.

Accordingly, what is needed is a device for the treatment and prevention of carpal tunnel syndrome which keeps the wrist and hand from drooping below the neutral position. Also needed is for the device to not impede movement and use of the hand and digits of the hand in directions unrelated to carpal tunnel syndrome. Moreover, the device should restrict opposition between the thumb and fifth digit. Additionally needed is for the device to be interchangeably usable with either the left hand or right hand. Further, the device should be comfortable to wear.

DESCRIPTION OF THE PRIOR ART

Applicant is aware of the following U.S. patents concerning wrist support devices.

| U.S. Pat. No. | Inventor | Issue Date | Title |
| --- | --- | --- | --- |
| 5,769,804 | Harris et al. | Jun. 23, 1998 | CARPAL TUNNEL SYNDROME WRIST BRACE |
| 5,746,707 | Donald Eck | May 5, 1998 | CARPAL TUNNEL SYNDROME EXTERNAL BRACE |
| 5,468,220 | Benjamin Sucher | Nov. 21, 1995 | CARPAL TUNNEL BRACELET |
| 5,417,645 | Roger Lemmen | May 23, 1995 | FLEXIBLE WRIST SPLINT FOR CARPAL TUNNEL SYNDROME TREATMENT |
| 5,385,537 | Mark Davini | Jan. 31, 1995 | SPLINT SYSTEM |
| 5,214,799 | John Fabry | Jun. 1, 1993 | PROTECTIVE GLOVE FOR THE PREVENTION OF CARPAL TUNNEL SYNDROME |
| 5,160,314 | Helena Peters | Nov. 3, 1992 | WRIST SUPPORT |
| 4,850,341 | Fabry et al. | Jun. 25, 1989 | GLOVE FOR PROPHYLAXIS OF CARPAL TUNNEL SYNDROME |
| 4,531,241 | Saul Berger | Jul. 30, 1985 | HAND GLOVE |

Harris et al., U.S. Pat. No. 5,769,804, discloses a carpal tunnel syndrome wrist brace to immobilize the wrist after carpal tunnel syndrome surgery. The brace includes a shell having first and second edges lined with a plurality of eyelets and both of the edges being connected together by a tongue stitched therebetween. The shell includes a thumb hole for receiving a thumb and is shaped to fit a patient's wrist such that the patient can insert the hand and wrist into the proximal end of the shell and extend four fingers through the distal end of the shell with the thumb through the thumb hole. The shell is then secured to the patient's wrist to activate immobilization of the wrist using a pair of hook and loop fasteners and a plurality of laces.

Eck, U.S. Pat. No. 5,746,707, teaches a wrist restraining device for the treatment of carpal tunnel syndrome wherein the device comprises a palmer brace which restrains the wrist, thumb and fifth digit, with unrestricted motion of the second, third, and fourth digits, to relieve pressure on the median nerve in the wrist.

Sucher, U.S. Pat. No. 5,468,220, provides a bracelet-like device for the treatment or prevention of carpal tunnel syndrome where the device includes a C-shaped member having a central portion located over the dorsal side of the wrist and two arms encircling the wrist. Each arm has a pad for engaging the palm near the attachment edges of the carpal ligament at the medial border and the lateral border of the carpal bones. The device also includes a pad attached to the central portion for engaging the dorsal part of the wrist.

Lemmen, U.S. Pat. No. 5,417,645, discloses a flexible splint for the treatment of carpal tunnel syndrome. The splint includes an elongate, flexible member having a palmer portion and an elongate proximal portion. The palmer portion has a curved sickle shape and defines a thumb notch. The palmer portion is angled with respect to the proximal portion to position the hand in a near normal anatomical position. Elastic straps attach the splint to the wrist and palm of the user.

Davini, U.S. Pat. No. 5,385,537, discloses a splint including a brace which cradles either the radius or the ulna of the wrist and an attachment strap which embraces the other two bones. The brace and the strap act to approximate the radius and the ulna toward one another to support the carpal tunnel without allowing compression of the anterior surface of the carpal tunnel.

Fabry, U.S. Pat. No. 5,214,799, teaches a glove for preventing carpal tunnel syndrome wherein the glove has a palm-covering padding which protects the wearer's hand. The pad is made of a resilient flexible material to provide protection from vibrations and shocks which can cause carpal tunnel syndrome. The glove also has a fold line extending diagonally across the palm to facilitate gripping the handle of an implement.

Peters, U.S. Pat. No. 5,160,314, teaches a wrist support adapted to be pulled onto and positioned about the hand and wrist area and adapted to anatomically conform to the wrist and basal hand of the wearer. The wrist support includes a sleeve constructed of a resilient elasticized fabric. The sleeve is provided with a thumb opening and means for receiving a palmar stabilizing stay, with the stay being removable. A compression strap is integral with the sleeve and extends around the wrist.

Fabrey et al., U.S. Pat. No. 4,850,341, discloses a glove for preventing carpal tunnel syndrome and includes a pad disposed therein for protecting the median nerve of a wearer's hand. The pad is secured to the glove and extends from the near the wrist opening of the glove to about the center of the portion of the glove which covers the palm. The pad is made of a resilient material to provide protection from vibrations and shocks.

Berger, U.S. Pat. No. 4,531,241, teaches a glove for the prevention of carpal tunnel syndrome. The glove includes a body having an outside pad and an inside cushion respectively secured to the outside and inside surfaces of the body. The glove terminates below the fingers and inside the thumb and fits over a major portion of the palm, wrist, and a portion of the forearm.

SUMMARY OF THE INVENTION

The present invention is a device for preventing and alleviating carpal tunnel syndrome. During normal operation, the invention is positioned across the wrist of the wearer to support the hand and wrist in the neutral position and to restrict motion of the wrist which is related to carpal tunnel syndrome. While worn, the device allows the wearer free motion of the wrist in the remaining directions, full use of the hand and digits of the hand, and a degree of comfort not provided for in prior devices. The carpal tunnel device is also universal such that it can be worn on either the right or left hand and fits a wide range of hand sizes.

In the broadest sense, the universal carpal tunnel device includes a palmar section for extending over a heel of a hand and terminating prior to a palmar fold of the hand, and a main section which extends from the palmar section for engaging the forearm of a wearer. A stay supports the palmar and main sections and extends along a longitudinal axis of the carpal tunnel device. The stay is generally linear along the longitudinal axis and along a transverse axis and is curvilinear in a direction normal to the axes to support the hand in a neutral position. Attachment means is provided for attaching the carpal tunnel device to the wearer. More preferably, the palmar section of the carpal tunnel device has a width capable of impeding opposition between a thumb and fifth digit of the hand by restricting flexion of a hypothenar eminence and a thenar eminence. Even more preferable, the palmar and main sections have a first half and a second half wherein the second half is substantially the mirror image of the first half so that the carpal tunnel device can be interchangeably worn on either the right or left hand. Most preferably, the carpal tunnel device has a center-line and the stay is positioned along the center line.

In the broadest sense, the present invention also relates to a universal carpal tunnel device for the treatment of carpal tunnel syndrome comprising a pad having a first side for placement against a wearer and a second side opposed to the first side, a base attached to the second side of the pad, and a stay disposed between the pad and the base. The pad and base have a palmar section for extending over a heel of a hand and terminating before a palmar fold of a hand of a wearer, and a main section extending from palmar section for engaging a forearm of the wearer. The stay supports the palmar and main sections and extends along a longitudinal axis of the carpal tunnel device. The stay is generally linear along the longitudinal axis and a transverse axis and is curvilinear in a direction normal to the axes to the support the hand in a neutral position. Attachment means is provided for attaching the carpal tunnel device to the wearer. More preferably, the base or the second side of the pad has a recessed channel in which the stay is disposed.

OBJECT OF THE INVENTION

The principal object of the present invention is to provide a device for the prevention and alleviation of carpal tunnel syndrome.

Another object of this invention is to provide an apparatus for supporting the wrist and hand in a neutral position.

A further object of this invention is to provide a device which does not impede movement of the hand and digits of the hand which is not associated with carpal tunnel syndrome.

Another object of this invention is to provide a device which restricts flexion of the hand between the hypothenar eminence and the center of thenar eminence.

Another object of this invention is to provide a device which can be worn on either the left or right hand, and on a wide range of hand sizes.

A further object of this invention is to provide a device which is comfortable to wear.

BRIEF DESCRIPTION OF THE DRAWINGS

The foregoing and other objects will become more readily apparent by referring to the following detailed description and to the appended drawings in which:

FIG. 2 is a perspective view of the device of FIG. 1 taken from the underside of the wearer's wrist;

FIG. 3 is a back view of the carpal tunnel device;

FIG. 4 is a front view of the carpal tunnel device;

FIGS. 5a, 5b, and 5c together comprise an exploded view of the carpal tunnel device; FIG. 5a is a perspective view of a base having a channel; FIG. 5b shows a stay which is disposed within the channel; and FIG. 5c shows the face pad;

FIG. 6 is a side view of the stay of FIG. 5;

FIGS. 7a, 7b, 7c, and 7d together comprise an exploded view of an alternative embodiment of the carpal tunnel device showing a base, a pad having a channel and a stay disposed within the channel; and FIGS. 8a, 8b, and 8c together comprise an exploded view of another embodiment of the carpal tunnel device showing a stay disposed between a base and pad, and wherein the stay is not disposed within a channel.

DETAILED DESCRIPTION

Figure 1:
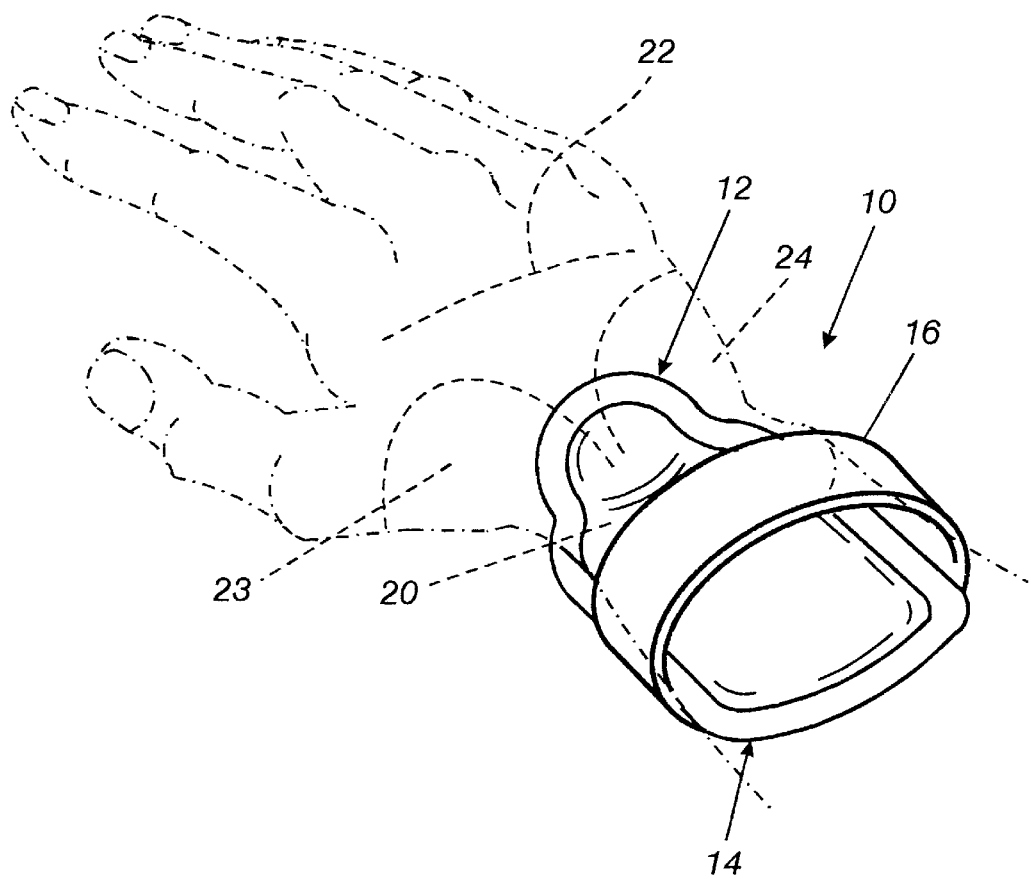
FIG. 1 is a perspective view of the invented universal carpal tunnel device in operating position attached to a wearer.

The present invention is a device for preventing and alleviating carpal tunnel syndrome. In particular, the present invention attaches at the wrist of a wearer to support the wrist and hand at about 15 degrees in a position called the neutral position. While worn, the device allows the wearer free motion of the wrist in directions unrelated to carpal tunnel syndrome, full use of the hand and digits of the hand, and a greater degree of comfort than provided in prior devices. Additionally, the carpal tunnel device is universal in configuration, whereby it can be worn on either the right hand or the left hand and it fits a wide variety of hand sizes.

Referring now to the drawings, and particularly FIGS. 1 and 2, the invented universal carpal tunnel device 10 includes a palmar section 12 for engaging the heel of a wearer's hand, a main section 14 extending rearward from the palmar section 12 for engaging the forearm of the wearer, and a means for removably attaching 16 the carpal tunnel device 10 to the wearer.

The main section 14 has a distal end 20 near or at the wrist-hand junction of the wearer and extends partially along the forearm of the wearer. The width of the main section is sufficient to comfortably cradle the forearm of the wearer.

The palmar section 12 tapers forward from the distal end 20 of the main section 14 and extends at least partially over the heel of the hand. Preferably, the palmar section 12 terminates prior to the palmar fold 22 of the hand. The palmar section 12 has sufficient width to provide support at or near the center of the thenar eminence 23 and at or near the center of the hypothenar eminence 24 to impede opposition between the thumb and fifth digit and accordingly prevent excess flexion therebetween.

FIGS. 3 and 4 respectively are front and back views of the carpal tunnel device 10. These views show the general contour of the palmar and main sections 12, 14 which supports the wearer's wrist and hand.

As shown in FIGS. 5a, 5b, and 5c, the carpal tunnel device 10 has a base 26 and a pad 28 which respectively form the inner and outer surfaces of the device 10. The base 26 and pad 28 are secured together by stitching, adhesive or other suitable means and enclose a stay 30 therebetween for supporting the hand and wrist of the wearer. The pad 28 can be made from any variety of material which provides cushioning and comfort when placed against a wearer's skin, such as polyurethane foam, open and closed cell foams, synthetic rubber and the like.

The base 26 is self-supporting, flexible and preferably made of #12 Volara closed cell foam. However, other materials are acceptable such as polyurethane, polyolefin, polyester, open and closed cell foams, neoprene, natural and synthetic rubbers, thermoplastic elastomers, silicones, plastics with a Shore hardness below 90, gels and laminated air cells.

The inward facing surface 32 of the base 26 is provided with a recessed channel 34 along its longitudinal center-line axis 36 for receiving the stay 30. The channel 34 is approximately the same size and configuration as the stay 30 such that the stay 30 is flush with the inward surface 32 of the base 26.

The stay 30, shown in FIGS. 5b, 7c and 8b is made of a rigid, moldable or resilient material such as metal or plastic and is positioned along the longitudinal center-line 36 of the carpal tunnel device 10. The stay 30 is generally linear along the longitudinal and transverse axes 36, 38 and curvilinear in a direction normal to the axes. Specifically, the stay 30 is configured to support the wearer's hand in the neutral position by having a proximal end 40 extending in a plane along the forearm of the wearer, a declined intermediate portion 42 and an inclined distal end 44 for supporting the wrist and heel of the hand. The distal end 44 extends over at least part of the heel of the hand and terminates before the palmar fold 22 (FIGS. 1 and 2) of the hand.

As illustrated in FIGS. 1 and 2, the width (W) of the stay 30 (the stay width is depicted in FIG. 5b) in combination with the base 26 and pad 28 provides the proper amount of support to restrict opposition between the thumb and fifth digit while being comfortable to wear. In particular, the stay 30 provides support along the middle of the wrist and heel of the hand. Since the pad and/or base 26 are self-supporting, that is semi-rigid yet flexible, they extend the area of support from the stay 30 to at or near the center of the hypothenar eminence and the thenar eminence.

FIG. 6 is a side view of the stay 30 and includes reference indicia which correspond to preferred range of stay 30 dimensions and more preferred dimensions as listed in Table 1 below. Although preferred dimensions are provided, the stay 30 may have other suitable dimensions.

TABLE 1

|  |  | Preferred Range | Preferred Range | More Preferred Range | More Preferred Range |
|---|---|---|---|---|---|
| Length | (L1) | 1 31/32"–2 11/16" | 5.0–6.8 cm | 2"–2 1/2" | 5.1–6.4 cm |
| Length | (L2) | 7/16"–1 1/8" | 1.1–2.9 cm | 1/2"–1" | 1.2–2.5 cm |
| Length | (L3) | 3/4"–1 5/16" | 1.9–3.3 cm | 7/8"–1 1/4" | 2.2–3.2 cm |
| Width | (W) | 1/2"–2" | 1.3–5.1 cm | 3/4"–1 1/4" | 1.9–3.2 cm |
| Stay Thickness | (T) | 1/32"–1/4" | 0.8–6.4 mm | 1/16"–1/8" | 1.6–3.2 mm |
| Down Angle | (A1) | 15°–30° |  | 20°–25° |  |
| Up Angle | (A2) | 20°–35° |  | 25°–30° |  |
| Distance | (D1) | 1/4"–1/2" | 6.4–12.7 mm | 3/8"–7/16" | 9.5–11.1 mm |
| Distance | (D2) | 3/8"–3/4" | 9.5–19.1 mm | 1/2"–5/8" | 1.3–1.6 cm |

Referring to FIGS. 5a, 5b, and 5c, the carpal tunnel device 10 is configured to be comfortable when worn. Since the stay 30 is positioned in the base channel 34, the cushioning pad 28 disposed between the stay 30 and the wearer, and the base 26 and /or pad are self-supporting, neither the ridge-line of the stay nor pressure points are felt by the wearer. Accordingly, the entire surface area of the carpal tunnel device 10 has a seamless feel while conforming to the wearer.

The carpal tunnel device 10 is also universally designed to be interchangeably compatible with the left and right hand. That is, the device 10 laterally has first and second sides which are mirror images of each other, with the stay 30 positioned along the longitudinal center-line 36.

Shown in FIGS. 1–4, the carpal tunnel device 10 includes attachment means 16 for securing the device 10 to the wearer. Preferable, the attachment means 16 is an adjustment strap secured to the base 26 and of suitable length to encircle the wrist of the wearer for releasable attachment (FIGS. 1, 3 and 4) by hook and loop means, such as sold under the trade name Velcro®. Preferably, a buckle 50 is secured to the proximal end of the adjustment strap 16 for the distal end to loop there-through. Other suitable attachment means can be used to secure the device 10 to the wearer.

FIGS. 7a, 7b, 7c, and 7d show an alternative embodiment of the universal carpal tunnel device 60 which generally has the same shape, utilizes the same stay 30, is configured for universal wear, has attachment means 16, and supports the wrist and hand of the wearer as described in the previous embodiment. That is, the device 60 in a substantially similar manner as illustrated in FIGS. 1 and 2, supports the wrist and hand at the neutral position by extending at least partially over the heel of the hand while terminating prior to the palmar fold of the hand and restricts opposition of the thumb and fifth digit by having a self-supporting palmar section 62 which seamlessly extends the area of support beyond the width of the stay 30.

The alternative device 10 includes a base 70 and pad 72 attached together with the stay 30 enclosed therebetween for supporting the wrist and hand of the wearer. The base 70 is formed of a wear-durable material such as leather, vinyl, and of the materials listed for the base of the previous embodiment and any suitable composite material.

The pad 72 preferably is formed of #12 Volara closed cell foam, but can be made of any suitable material such as those listed in the previous embodiment for the base 26. A recessed channel 74 is provided in the outward facing 76 surface of the pad 72. The channel 74 is generally the same shape and size as the stay 30 and the stay 30 is as described in the previous embodiment. Preferable, a liner 78 such as soft fabric is attached to an inward facing surface 80 of the pad 72 to provide a comfortable feel for the wearer.

Another embodiment of the carpal tunnel device 90 is shown in FIGS. 8a, 8b, and 8c. This embodiment is substantially the same shape, utilizes the same stay 30, is configured for universal wear, has attachment means such as the strap 16, and supports the wrist and hand of the wearer as described in the previous embodiments. The objectives of the device 90 are met by securing the stay 30 between a base 94 and pad 96, along a longitudinal center-line axis 98 of the carpal tunnel device 90, but without providing a channel for housing the stay 30. With the channel-less construction, it is preferable that the base 94 and/or pad 96 be made of a material which displaces, such as air cells and foams, as opposed to materials that compress such as silicones. Use of the displacing material eliminates stay ridge-lines and pressure points to create a seamless feel to the wearer of the carpal tunnel device 90.

In use, and referring to FIGS. 1 and 2, the wearer attaches the universal carpal tunnel device 10 onto either the right or left hand. The attachment means 16 is encircled around the wearer's forearm, inserted through the buckle 50 (FIG. 2) and pulled to desired tightness to secure the device 10 to the wearer. When tightening, the lateral edges of the base 26 and pad 28 secure the device 10 to the wearer and conform about the wearer's forearm. Since the stay 30 is sufficiently narrow, the stay does not interfere with the carpal tunnel device 10 conforming to the wearer.

When the carpal tunnel device 10 is positioned to the wearer, the downward and upward angles of the stay 30 support the wrist and hand in the neutral position and prevent drooping of the wrist. The stay 30 is also sufficiently wide so that, in combination with the base 26 and pad 28, the palmar section 12 rests partially over the fatty pads of the hypothenar eminence to prevent excessive opposition. Moreover, the carpal tunnel device 10 terminates prior to the palmar fold 22 of the wearer's hand and does not require attachement means about the back of the hand. Consequently, the wearer has full use of the hand in movement unrelated to carpal tunnel syndrome.

SUMMARY OF THE ACHIEVEMENT OF THE OBJECTS OF THE INVENTION

From the foregoing, it is readily apparent that I have invented an universal carpal tunnel wrist support device for alleviating and preventing carpal tunnel syndrome. The universal wrist support device can be worn on either the left or right hand, maintains the hand at the neutral position, supports the hand at the proper typing height, and does not unnecessarily restrict movement of the hand and digits of the hand which are unrelated to carpal tunnel syndrome.

It is to be understood that the foregoing description and specific embodiments are merely illustrative of the best mode of the invention and the principles thereof, and that various modifications and additions may be made to the apparatus by those skilled in the art, without departing from the spirit and scope of this invention.

What is claimed:

1. A universal carpal tunnel device that is interchangeably compatible with the left and right hand having longitudinal and transverse axes for the treatment of carpal tunnel syndrome, comprising:
    a palmar section having a distal end configured to terminate before the palmar fold of a hand of a wearer and a proximal end;
    a main section extending from the proximal end of said palmar section for engaging a forearm of the wearer;
    a stay supporting said palmar and main sections and extending along the longitudinal axis of said carpal tunnel device, wherein said stay is generally linear along the longitudinal and transverse axes and is curvilinear adjacent to the palmar section therein providing directional support for the hand in a neutral position; and
    means for attaching said carpal tunnel device to the wearer.

2. The carpal tunnel device according to claim 1 wherein said palmar section has a width capable of impeding opposition between a thumb and a fifth digit of the hand by restricting flexion of the hypothenar eminence and the thenar eminence.

3. The carpal tunnel device according to claim 2 wherein said palmar section is adapted to contact the hand generally at a center of the hypothenar eminence and generally at a center of the thenar eminence.

4. The carpal tunnel device according to claim 1 wherein the distal end of said palmar section is configured to terminate at the heel of the hand.

5. The carpal tunnel device according to claim 1 wherein said carpal tunnel device, laterally, has first and second sides that are substantially mirror images of each other.

6. The carpal tunnel device according to claim 1 wherein said attachment means is a single strap for wrapping about the forearm having a first end secured to said main section and a second end that is releasably attachable to itself or another part of said strap.

7. The carpal tunnel device according to claim 1 wherein the longitudinal axis is a longitudinal center-line of said carpal tunnel device and said stay is positioned along the longitudinal axis.

8. The carpal tunnel device according to claim 7 wherein said stay has a width in the range of about ½ inch to 2 inches (1.3 cm to 5.1 cm).

9. The carpal tunnel device according to claim 7 wherein the width of said stay is about ¾ inch to 1¼ inches (1.9 cm to 3.2 cm).

10. The carpal tunnel device according to claim 8 wherein said stay has a proximal end positioned in a plane, a declined intermediate portion extending from said proximal end of said stay and terminating in the range of about ¼ inch to ½ inch (6.4 mm to 12.7 mm) to one side of the plane, and an inclined distal end extending from said intermediate portion and terminating in the range of about ⅜ inch to ¾ inch (9.5 mm to 19.1 mm) to an opposing side of the plane.

11. The carpal tunnel device according to claim 10 wherein said intermediate portion is adapted to positioned at a wrist-heel junction of the wearer and to extend partially across a heel of the hand for preventing drooping of the wrist, and wherein said distal end extends across the remainder of the heel for supporting the hand in the neutral position.

12. A universal carpal tunnel device that is interchangeably compatible with the left and right hand having longitudinal and transverse axes for the treatment of carpal tunnel syndrome, comprising:
    a pad having a first side for placement against a wearer and a second side opposed to the first side;
    a base attached to the second side of said pad;
    wherein said pad and said base in combination include:
        a palmar section having a distal end configured to terminate before the palmar fold of a hand of the wearer and a proximal end, and
        a main section extending from the proximal end of said palmar section for engaging a forearm of the wearer;
    a stay disposed between said pad and said base, supporting said palmar and main sections, and extending along the longitudinal axis of said carpal tunnel device, wherein said stay is generally linear along the longitudinal and transverse axes and is curvilinear adjacent to the palmar section therein providing directional support for the hand in a neutral position; and
    means for attaching said carpal tunnel device to the wearer.

13. The carpal tunnel device according to claim 12 wherein said base has a recessed channel and said stay is disposed in said recessed channel.

14. The carpal tunnel device according to claim 13 wherein said recessed channel and said stay have approximately the same dimensions.

15. The carpal tunnel device according to claim 12 wherein the second side of said pad has a recessed channel and said stay is disposed in said recessed channel.

16. The carpal tunnel device according to claim 15 wherein said recessed channel and said stay have approximately the same dimensions.

17. The carpal tunnel device according to claim 12 wherein said carpal tunnel device is self-supporting in shape and wherein the main section is adapted to resiliently conform to the forearm of the wearer.

18. The carpal tunnel device according to claim 17 wherein said palmar section has a width greater than a width of said stay, and wherein said palmar section is capable of impeding opposition between a thumb and a fifth digit of the wearer by restricting flexion of a hypothenar eminence and the thenar eminence.

19. The carpal tunnel device according to claim 18 wherein said palmar section is adapted to contact the hand generally at a center of the hypothenar eminence and generally at a center of the thenar eminence.

20. The carnal tunnel device according to claim 17 wherein said carpal tunnel device, laterally, has first and second sides that are substantially mirror images of each other, and wherein said attachment means is a single strap for wrapping about the forearm having a first end secured to said main section and a second end releasably attachable to itself or another part of said strap.

* * * * *